United States Patent [19]
Shiga et al.

[11] Patent Number: 5,891,660
[45] Date of Patent: Apr. 6, 1999

[54] METHOD OF INHIBITING THE ACTIVITY OF THE REDUCING SUBSTANCES IN OXIDATIVE CHROMOGENIC ANALYSIS

[75] Inventors: Masanobu Shiga; Makoto Mizoguchi, both of Kumamoto; Kazumi Sasamoto, Kamimashiki-gun, all of Japan

[73] Assignee: Dojindo Laboratories, Kumammoto Prefecture, Japan

[21] Appl. No.: 644,589

[22] Filed: May 10, 1996

[51] Int. Cl.⁶ ........................................... C12Q 1/54
[52] U.S. Cl. .................. 435/14; 435/27; 435/28
[58] Field of Search ................... 435/14, 28, 27

[56] References Cited

U.S. PATENT DOCUMENTS

| | | | |
|---|---|---|---|
| 4,168,205 | 9/1979 | Danninger et al. | 435/10 |
| 4,921,962 | 5/1990 | Galbo et al. | 546/184 |
| 5,380,650 | 1/1995 | Barnard et al. | 435/28 |

FOREIGN PATENT DOCUMENTS

| | | |
|---|---|---|
| 0 016 962 | 7/1982 | European Pat. Off. . |
| 754760 | 1/1997 | European Pat. Off. . |
| Sho-63/ 049081 | 3/1988 | Japan . |

OTHER PUBLICATIONS

N. Takahashi et al., J. Pesticide Sci. vol. 13, pp. 429–435 (1988).

A. Samuni et al., J. Clin. Invest. vol. 87, No. 5, pp. 1525–1530 (1991).

K. Moore et al., Archives of Biochemistry and Biophysics, vol. 299, No. 1, pp. 47–56 (Nov. 1992).

*Primary Examiner*—Mary E. Ceperley
*Attorney, Agent, or Firm*—Graham & James LLP

[57] ABSTRACT

An object of the present invention is to inhibit the influence of the reducing substances on the oxidative coloring reaction in biological components.

A constitution of the present invention is that a compound having the free radical of the general formula (1)

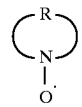

is previously added to the biological sample and then an incubation is carried out.

An effect of the present invention is that the influence of the reducing substances on the oxidation reaction can be inhibited and, even when no reducing substance is present, there is no effect on the oxidation reaction.

5 Claims, 2 Drawing Sheets

METHOD OF INHIBITING THE ACTIVITY OF THE REDUCING SUBSTANCES IN OXIDATIVE CHROMOGENIC ANALYSIS

DETAILED DESCRIPTION OF THE INVENTION

1. Technical Field

The present invention relates to a method of removing the reducing substances in biological components in a diagnostic analysis and, more particularly, it relates to a method of inhibiting the activity of the reducing substances wherein the reducing substances which can be a cause for an error due to inhibition of coloring in the case of utilizing the oxidative chromogenic reaction are made to selectively react with a certain compound followed by removing it from the system.

2. Prior Art

For detecting the only desired component in a selective manner from a very complicated matrix in a selective detection of biological components in blood and urine, enzymatic analysis using glucose oxidase, cholesterol oxidase, uricase or various dehydrogenases or enzyme substrate for measuring the enzymatic activity of the biological sample have been widely used at present. Among them, a method using various oxidases are now an inevitable means for daily tests.

Usually, hydrogen peroxide which is produced by oxidation of the substrate (which is an object for the measurement) with various oxidases can be easily determined by means of a spectroscopic analysis by the reaction with an oxidative chromogenic substrate in the presence of catalase or peroxidase.

As compared with a measuring method utilizing chemical reactions, the above-mentioned enzymatic analysis method has a specificity and the reaction proceeds under a mild condition independently of the type of the enzyme. Accordingly, many components can be measured under the same analytical conditions whereby such a method can be easily automated. Thus, it is likely that said method will spread more and more in future when the significance of measurement of the components in clinical area is made clear.

PROBLEMS TO BE SOLVED BY THE INVENTION

It has been known, however, that hydrogen peroxide is consumed by various reducing substances which exist in the biological samples resulting in a negative error especially in an oxidative enzymatic reaction using a system of peroxidase and hydrogen peroxide.

Among such reducing substances, ascorbic acid is a compound which is a cause of the biggest problem. With a boom for healthy drinks in recent years, beverages and food to which a large amount of ascorbic acid is added have been increasing. Therefore, it is likely that such an interference is more and more increasing.

It is desirable to remove the reducing substances such as ascorbic acid by a simple pretreatment. However, addition of oxidative metal salts or organic substances which have been attempted up to now results in a reaction not only with those interfering substances but also with oxidative coloring substrate causing a positive error. Therefore, they cannot be used in a reaction system using an oxidative coloring dye.

An object of the present invention is to offer a method of inhibiting the activity of the reducing substances in which a certain compound is used whereby it selectively reacts with the reducing substances in the biological sample eliminating their interference and, in addition, it does not affect the reaction system comprising peroxidase or catalase and hydrogen peroxide.

MEANS TO SOLVE THE PROBLEMS

The present inventors have conducted intensive studies and, as a compound which inhibits the activity of the reducing substance in the biological sample, they have found a compound having a free radical of the following formula (1).

(1)

(in the formula, R is a cyclic alkyl group which has 4 or 5 carbon atoms or a cyclic alkyl group which may have one double bond and it may have substituent(s) such as alkyl, amino, amide, carbamoyl, carboxyl, keto, hydroxyl, sulfonic acid and phenyl groups or the carbon atom of the cyclic alkyl group may be substituted with nitrogen atom, oxygen atom, sulfur atom and the like).

Unlike the usual oxidizing agents such as metal salts, the stable radical in the molecule of the above-mentioned compound acts with a reducing substance such as ascorbic acid and changes to a hydroxyl substance of the following formula (2).

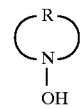

(in the formula, R has the same meaning as that in the compound (1)).

In an oxidation reaction of the reducing substances using such an organic radical, it does not participate at all in an oxidative coloring reaction by means of peroxidase and hydrogen peroxide which have been used in conventional measurements while the coloring sensitivities depending upon the hydrogen peroxide concentration and reaction rate in the oxidative coloration show the same values.

With regard to the organic radical of the above-mentioned formula (1) used in the present invention, several kinds of organic radicals have been commercially available already and their general synthetic methods are shown by a method of A. M. Feldman, et al. (U.S. Pat. No. 3,334,103) and a method of W. Bueschken, et al. (German Patent No. 4,219, 459). An amine to be treated is oxidized in ether using benzoyl peroxide. Water is added to that compound to decompose and sodium hydroxide/aqueous methanol are added thereto followed by heating to reflux to give a hydroxylamine. Said compound is then oxidized in the presence of a base to give a desired radical. With respect to the compounds which have not be commercially available, their synthetic examples will be given later.

Examples of the compound which is capable of inhibiting the activity of the reducing substances in accordance with the present invention will be given as hereunder. The alkyl group which is other than the alkyl chain participating in the ring structure is a methyl group and, especially when methyl groups are substituted with carbon atoms connecting to the nitrogen atom, stabilization of the radical can be achieved. Functional groups such as alkyl, alkoxy, amino, carboxyl, carbamoyl, hydroxyl, sulfhydryl, phenyl, amide, etc. may be added thereto as substituent(s).

(A) 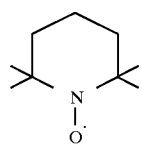

(B) 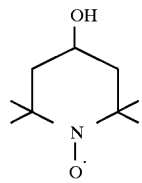

(C) 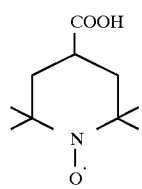

(D) 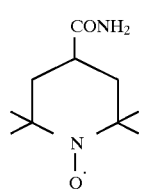

(E) 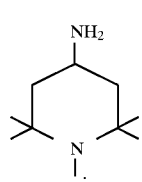

(F) 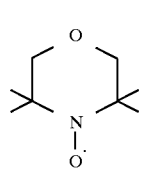

(G) 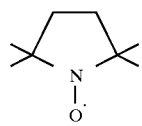

(H) 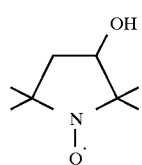

(I) 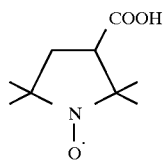

-continued (J) 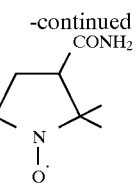

(K) 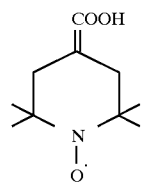

(L) 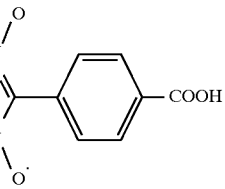

EXAMPLES

The present invention will now be further illustrated by way of the following examples which, however, do not limit the scope of the present invention thereto.

SYNTHETIC EXAMPLE 1

Synthesis of the Compound (D)

A compound (C) (20 g; 99.9 mmoles) was dissolved in 500 ml of tetrahydrofuran, cooled at 0° C., 30.9 g (0.149 mmole) of dicyclohexylcarbodiimide was added thereto little by little and the resulting mixture was stirred for 30 minutes. Ammonia gas was blown thereinto and the resulting mixture was stirred for three hours. The reaction solution was concentrated in vacuo and the residue was purified by means of a column chromatography (silica gel; 2% methanol/chloroform) to give 18.5 g (yield: 93%) of the desired product.

SYNTHETIC EXAMPLE 2

Synthesis of the Compound (F)

2,2,6,6-Tetramethylmorpholine (4 g; 27.7 mmoles) was dissolved in 200 ml of chloroform, 9.56 g (55.4 mmoles) of m-chloroperbenzoic acid was added and the mixture was stirred for two hours at room temperature. The reaction solution was filtered and the filtrate was washed with 2% aqueous solution of sodium bicarbonate for three times, dried over anhydrous magnesium sulfate and filtered. The filtrate was concentrated in vacuo, the solid separated out therefrom was dissolved in benzene and the solution was filtered through a column of silica gel to give 3.28 g (yield: 75%) of the desired compound. This was in yellow crystals. Melting point was 78°–80° C. Elementary analysis: C=60.55%, H=9.98%, N=8.90%; calculated: C=60.73%, H=10.19%, N=8.85%.

EXAMPLE 1

Influence of the Removing Agent for Reducing Substances in Biological Samples in the Coloring Reaction using TOOS.

(Coloring Solution)

0.1M phosphate buffer solution (pH: 7.4) (1 ml) containing 1 mM of N-(2-hydroxy-3-sulfopropyl)-N-ethyl-3-methylaniline (TOOS) was mixed with 1 ml of 0.1M phosphate buffer (pH: 7.4) containing 1 mM of 4-aminoantipyrine (4-AA) and 0.1 ml of 0.1M phosphate buffer (pH: 7.4) containing 10 U/ml of peroxidase and then 0.1M phosphate buffer (pH: 7.4) was added to make total volume 2.89 ml.

(Hydrogen Peroxide Solution)

Commercially available aqueous solution of hydrogen peroxide was dissolved in 0.1M phosphate buffer (pH: 7.4) and an adjustment was conducted to make the final concentration 10 mM.

(Solution of Activity Inhibitor for Reducing Substances)

Each of the compounds B, C and J was dissolved in 0.1M phosphate buffer (pH: 7.4) and an adjustment was conducted to make the concentration 10 mM.

(Operation Method)

A solution of the activity inhibitor for the reducing substances (0.1 ml) was added to a coloring solution, incubated for five minutes at 37° C., 10 μl of hydrogen peroxide solution was added, the mixture was quickly stirred and, from that time, absorption at 555 nm was monitored by a spectrophotometer and the result was compared with that for the case where the solution of the activity inhibitor for the reducing substances was not added.

Results of the measurement are given in FIG. 1. From the results, it is apparent that the product of the present invention does not affect the usual oxidative coloration reaction at all.

EXAMPLE 2

Reduction of Influence of Ascorbic Acid in Coloring Reaction using TOOS (Coloring Solution)

0.1M Phosphate buffer (pH: 7.4) (1 ml) containing 1 mM of TOOS was mixed with 1 ml of 0.1M phosphate buffer (pH: 7.4) containing 1 mM of 4-AA and 0.1 ml of 0.1M phosphate buffer (pH: 7.4) containing 10 U/ml of peroxidase and then 0.1M phosphate buffer (pH: 7.4) was added thereto to make 2.89 ml.

(Ascorbic Acid Solution)

Commercially available sodium ascorbate was dissolved in 0.1M phosphate buffer and an adjustment was conducted to make the final concentration 10 mM.

(Hydrogen Peroxide Solution)

Commercially available aqueous solution of hydrogen peroxide was dissolved in 0.1M phosphate buffer (pH: 7.4) and an adjustment was conducted to make the final concentration 10 mM.

(Solution of Activity Inhibitor for Reducing Substances)

Each of the compounds B, C and J was dissolved in 0.1M phosphate buffer (pH: 7.4) and an adjustment was conducted to make each concentration 10 mM.

(Operation Method)

Each 0.1 ml of the solutions of the activity inhibitors for reducing substances was added to 20 μl of ascorbic acid solution. After that, incubation was conducted for five minutes, then 2.89 ml of a coloring solution and 10 μl of aqueous solution of hydrogen peroxide were added and the changes in the absorbances at 555 nm after five minutes were measured. As a control for comparison, changes in the absorbances for the case where no activity inhibitor solution for the reducing substances was added under the above-mentioned conditions were measured too.

Results of the measurement are given in FIG. 2. When a solution of the activity inhibitor for the reducing substances was not added, a significant influence by ascorbic acid was noted whereby coloration was inhibited while, when such solutions of the activity inhibitor for the reducing substances were added, influence by ascorbic acid was not noted at all except the case of the compound J whereupon it is apparent that the activity of ascorbic acid which reductively inhibits the oxidative coloring reaction is inhibited.

EXAMPLE 3

Measurement of Glucose in Blood Using the Inhibitor for Activity of the Reducing Substances (Coloring Solution)

One ml of 0.1M phosphate buffer (pH: 7.4) containing 1 mM of TOOS was mixed with 1 ml of 0.1M phosphate buffer (pH: 7.4) containing 10 U/ml of peroxidase and 0.1 ml of 0.1M phosphate buffer (pH: 7.4) containing 5 U/ml of glucose oxidase and then 0.1M phosphate buffer (pH: 7.4) was added thereto to make 3.0 ml.

(Solution of Activity Inhibitor for the Reducing Substances)

The compound B was dissolved in 0.1M phosphate buffer (pH: 7.4) and an adjustment was conducted to make the concentration 10 mM.

(Serum)

Deproteinized human serum (20 μl) was used. Sample I (male of 26 years old); sample II (male of 30 years old); sample III (male of 33 years old); sample IV (male of 35 years old); sample V (male of 39 years old); and sample VI (female of 26 years old).

(Operation Method)

To each 20 μl of the serum was added 10 μl of a solution of the activity inhibitor (the compound B) for the reducing substances, the mixture was allowed to stand at room temperature for five minutes, then 3 ml of a coloring solution which was previously warmed at 30° C. was added, the mixture was incubated at 30° C. for ten minutes and the absorbances at 555 nm were measured using a blank containing no reagent as a control. The measured data were compared with a working curve and the glucose concentration in the serum was determined. For comparison, the results for the serum which was not treated with a solution of the activity inhibitor for the reducing substances were measured. The results are given in Table 1.

TABLE 1

| Samples | Concentration of Glucose Treated with Solution of Activity Inhibitor for Reducing Substances | Concentration of Glucose Untreated with Solution of Activity Inhibitor for Reducing Substances |
|---|---|---|
| I | 85.2 (mg/dl) | 80.8 (mg/dl) |
| II | 73.2 | 72.9 |
| III | 94.9 | 88.8 |
| IV | 90.3 | 88.0 |

TABLE 1-continued

| Samples | Concentration of Glucose Treated with Solution of Activity Inhibitor for Reducing Substances | Concentration of Glucose Untreated with Solution of Activity Inhibitor for Reducing Substances |
|---|---|---|
| V | 79.4 | 77.1 |
| VI | 68.8 | 67.3 |

It is apparent that, when the glucose concentrations in the case where the serum was not treated with the compound B were compared with the case where the serum was treated with the compound B, the samples without such a treatment contained low glucose concentrations in general. Such a result is believed to be due to the presence of the reducing substances in the blood. Thus, when an agent which inhibits the activity of the reducing substances is used, precise concentration of glucose in blood can be determined without interference.

MERIT OF THE INVENTION

The agent of the present invention which inhibits the activity of the reducing substances acts with the reducing substances which affect the oxidative coloring reaction to inhibit the influence. Still it does not affect the usual oxidative coloration reaction at all.

Figure 1:
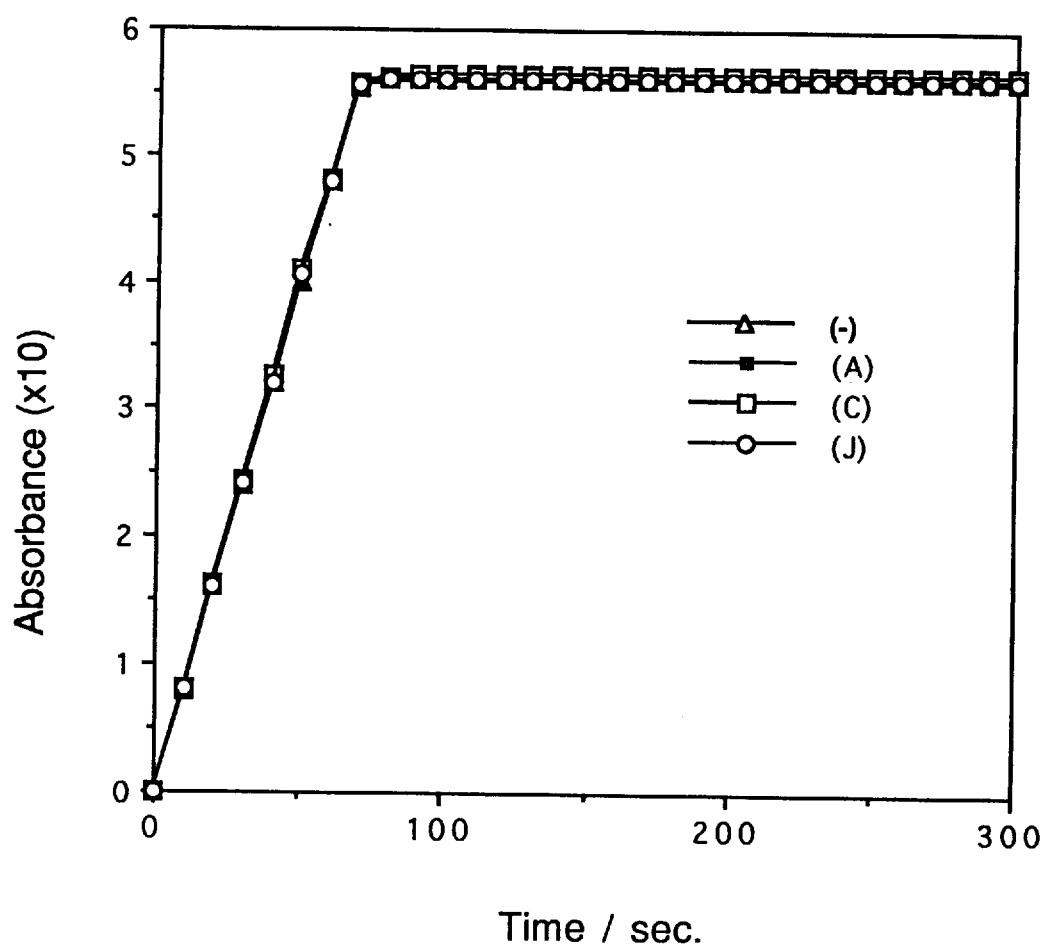
FIG. 1 shows the effect of the product of the present invention on the oxidative coloring reaction of a system comprising TOOS and 4-AA in which the abscissa is time (seconds) while the ordinate is absorbance at 555 nm. Incidentally, the curve with a triangular mark shows the normal changes in the absorbance when none of the product of the present invention was added.
Figure 2:
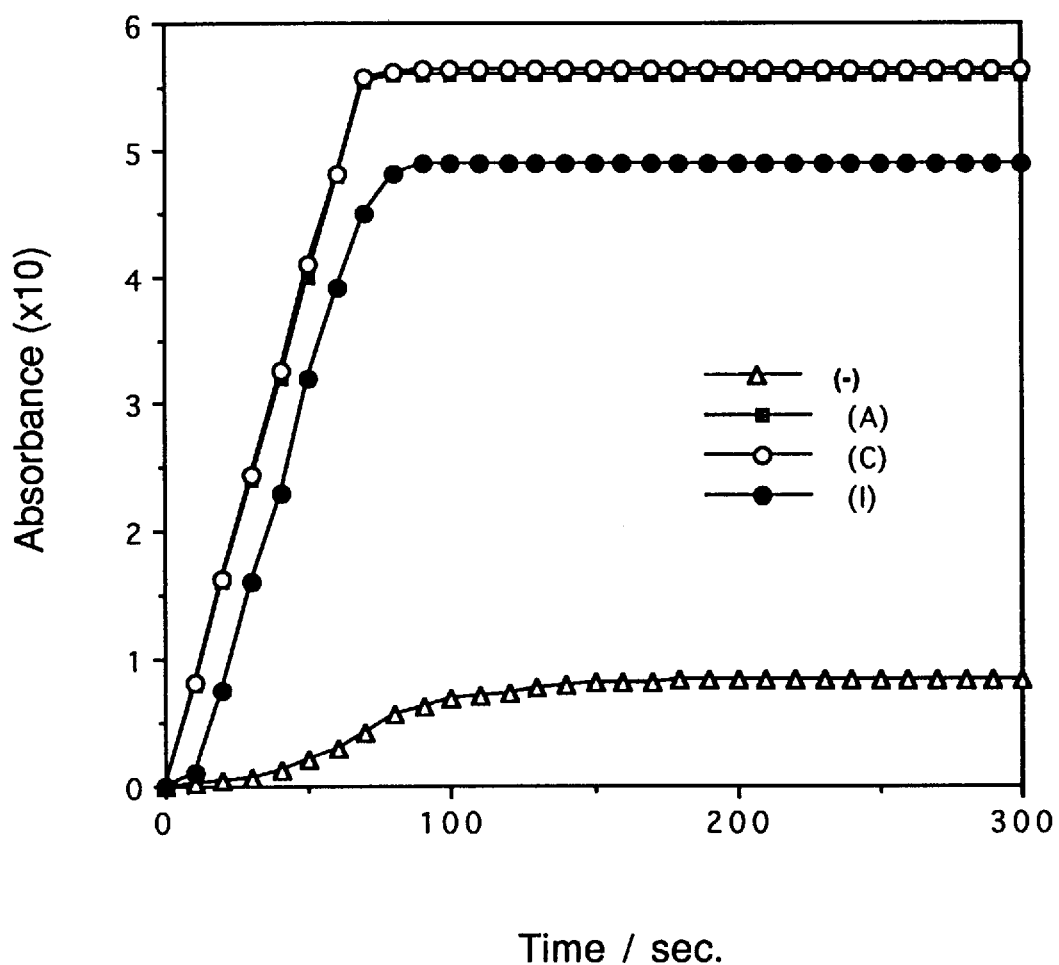
FIG. 2 shows the changes in absorbances when the compounds B, C and J were added for removing the ascorbic acid which was an inhibitor for the oxidative coloration reaction in a system comprising TOOS and 4-AA in which the abscissa is time (seconds) while the ordinate is absorbance at 555 nm. Incidentally, the curve with a triangular mark shows the effect of ascorbic acid when no activity inhibitor for the reducing substances was added.

We claim:

1. In a diagnostic analysis utilizing an oxidative chromogenic reaction, a method of inhibiting activity of reducing substances present during said reaction, which reducing substances cause inhibition of coloring used for diagnostic analysis, said method comprising the step of using a compound to selectively react with the reducing substances to thereby inhibit said activity, without otherwise participating in the oxidative chromogenic reaction, said compound having a free radical represented by the following formula (1)

(in the formula, R is a cyclic alkyl group which has 4 or 5 carbon atoms or a cyclic alkyl group which may have one double bond and it may have at least one substituent selected from alkyl, amino, amide, carbamoyl, carboxyl, keto, hydroxyl, sulfonic acid and phenyl groups or one of the carbon atoms of the cyclic alkyl group may be replaced by a heteroatom selected from nitrogen, oxygen, and sulfur atoms).

2. The method according to claim 1, wherein

is a piperidinyl or substituted piperidinyl.

3. The method according to claim 1, wherein the compound used is

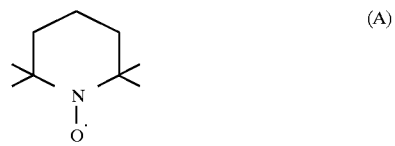

4. The method of according to claim 1, wherein the compound used is

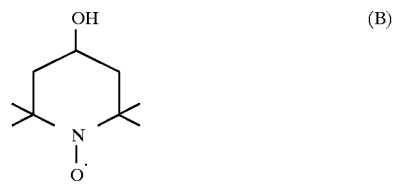

5. The method according to claim 1, wherein the compound used is

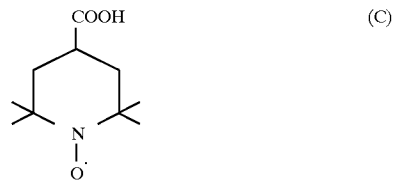

* * * * *